(12) United States Patent
Oba et al.

(10) Patent No.: US 12,134,760 B2
(45) Date of Patent: Nov. 5, 2024

(54) CHANNEL DEVICE (71) Applicant: FUJIFILM Corporation, Tokyo (JP)

(72) Inventors: Takahiro Oba, Ashigara-kami-gun (JP); Takahiro Ogura, Ashigara-kami-gun (JP); Koju Ito, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1032 days.

(21) Appl. No.: 17/002,384

(22) Filed: Aug. 25, 2020

(65) Prior Publication Data

US 2020/0385664 A1 Dec. 10, 2020

Related U.S. Application Data (63) Continuation of application No. PCT/JP2019/006670, filed on Feb. 22, 2019.

(30) Foreign Application Priority Data

Feb. 26, 2018 (JP) ................................ 2018-031757

(51) Int. Cl.
*C12M 1/12* (2006.01)
*G01N 21/64* (2006.01)
(Continued)

(52) U.S. Cl.
CPC ........... *C12M 25/02* (2013.01); *G01N 21/645* (2013.01); *G01N 27/07* (2013.01); *G01N 33/5005* (2013.01); *G01N 2021/6482* (2013.01)

(58) Field of Classification Search
CPC ................... C12M 25/02; C12M 35/00; B01L 2200/0668; B01L 2300/0645;
(Continued)

(56) References Cited

U.S. PATENT DOCUMENTS

2007/0099307 A1 5/2007 Woolverton
2009/0149345 A1 6/2009 Nishi et al.
(Continued)

FOREIGN PATENT DOCUMENTS

CN 101137908 A 3/2008
CN 102156158 A 8/2011
(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2019/006670, dated Sep. 3, 2020, with an English translation.
(Continued)

*Primary Examiner* — Lydia Edwards
(74) *Attorney, Agent, or Firm* — Birch, Stewart, Kolasch & Birch, LLP (57) ABSTRACT

An object is to provide a channel device that can perform both optical measurement and electrical measurement. The object is achieved by having a first channel member having a first channel, a second channel member having a second channel, a porous membrane provided between the first channel member and the second channel member, and a pair of transparent electrodes provided so as to interpose the first channel and the second channel therebetween.

9 Claims, 5 Drawing Sheets

(51) Int. Cl.
 G01N 27/07 (2006.01)
 G01N 33/50 (2006.01)
(58) Field of Classification Search
 CPC ..... B01L 2300/0681; B01L 2300/0887; B01L 3/502715; B01L 3/502761; G01N 2021/6482; G01N 21/05; G01N 21/645; G01N 27/07; G01N 33/5005; G01N 37/00
 See application file for complete search history.

(56) References Cited

U.S. PATENT DOCUMENTS

| | | | |
|---|---|---|---|
| 2010/0006774 | A1 | 1/2010 | Ohtsuka et al. |
| 2010/0194410 | A1 | 8/2010 | Ford et al. |
| 2011/0250585 | A1 | 10/2011 | Ingber et al. |
| 2012/0190040 | A1 | 7/2012 | Talebpour et al. |
| 2012/0219490 | A1 | 8/2012 | Noda et al. |
| 2012/0245053 | A1 | 9/2012 | Shirai et al. |
| 2014/0004501 | A1 | 1/2014 | Talebpour et al. |
| 2015/0107998 | A1 | 4/2015 | Fobel et al. |
| 2018/0320125 | A1 * | 11/2018 | Levner .................. C12M 35/08 |

FOREIGN PATENT DOCUMENTS

| | | | | |
|---|---|---|---|---|
| CN | 106513066 | A | 3/2017 | |
| CN | 107442188 | A | 12/2017 | |
| GB | 2467338 | A | 8/2010 | |
| JP | 2010-19766 | A | 1/2010 | |
| JP | 2010-185872 | A | 8/2010 | |
| JP | 2011-528232 | A | 11/2011 | |
| JP | 2012-194020 | A | 10/2012 | |
| JP | 2014-55979 | A | 3/2014 | |
| JP | 2015-138127 | A | 7/2015 | |
| JP | 2015-145340 | A | 8/2015 | |
| JP | 2018-11590 | A | 1/2018 | |
| TW | 201348121 | A | 12/2013 | |
| WO | WO 2011/068088 | A1 | 6/2011 | |
| WO | WO 2013/086502 | A1 | 6/2013 | |
| WO | WO 2017/096297 | A1 | 6/2017 | |
| WO | WO-2017106727 | A1 * | 6/2017 | ........ B01L 3/502707 |

OTHER PUBLICATIONS

International Search Report (Form PCT/ISA/210) for International Application No. PCT/JP2019/006670, dated May 14, 2019.
Extended European Search Report, dated Mar. 18, 2021, for corresponding European Application No. 19756838.9.
Taiwanese Office Action and Search Report for corresponding Taiwanese Application No. 108106275, dated Oct. 26, 2022, with a partial English translation.
Canadian Office Action and Search Report for corresponding Canadian Application No. 3,092,214, dated Sep. 17, 2021.
Chinese Office Action and Search Report for corresponding Chinese Application No. 201980015197.7, dated Nov. 22, 2022, with an English translation.
Canadian Office Action and Search Report for corresponding Canadian Application No. 3092214, dated Jul. 29, 2022.
Japanese Office Action dated Feb. 2, 2021, issued in corresponding Japanese Patent Application No. 2020-501051.
Chinese Office Action for corresponding Chinese Application No. 201980015197.7, dated Nov. 30, 2023, with English translation.
Chinese Office Action for corresponding Chinese Application No. 201980015197.7, dated Jul. 28, 2023, with a partial English translation.

* cited by examiner

CHANNEL DEVICE

CROSS-REFERENCE TO RELATED APPLICATIONS

This application is a Continuation of PCT International Application No. PCT/JP2019/006670 filed on Feb. 22, 2019, which claims priority under 35 U.S.C. § 119(a) to Japanese Patent Application No. 2018-031757 filed on Feb. 26, 2018. The above application is hereby expressly incorporated by reference, in its entirety, into the present application.

BACKGROUND OF THE INVENTION

1. Field of the Invention

The present invention relates to a channel device used for pharmaceutical research and the like.

2. Description of the Related Art

In recent years, it has been attempted to use a channel device having a channel with a width of micrometer order called a micro channel as an organ model of a blood vessel, an intestinal tract, a liver, a lung, or the like.

For example, JP2011-528232A discloses a channel device (an organomimetic device having a micro channel) including a body which has a central micro channel (micro channel) therein and an at least partially porous membrane positioned within the central micro channel, in which the porous membrane is configured to separate the central micro channel to form a first central micro channel and a second central micro channel, a first fluid flows through the first central micro channel and a second fluid flows through the second central micro channel, and a plurality of cells (living cells) are fixed to the porous membrane.

In the channel device, an air, a blood, water, cells, compounds, particles, a culture solution, and the like are caused to flow through the first central micro channel and the second central micro channel in a state where cells are fixed to the porous membrane. As a result, various analyzes can be performed on the porous membrane that reproduces an organ.

As an example, by causing a fluorescently labeled large molecule (for example, a dextran having a different weight) to flow through a micro channel and measuring the fluorescence, permeability of a cell layer formed on a porous membrane can be evaluated.

In addition, by causing a liquid to flow through a micro channel and imaging (visualizing) cells on a porous membrane using a transmission electron microscope, immunohistocytochemistry, a confocal microscope, or other appropriate means, a structure of a cell layer or the like formed on the porous membrane can be evaluated.

Furthermore, by using an electrode, infrared or photodetection means (camera and light emitting diode (LED)), magnetic detection means, or the like as a sensor, a characteristic and a state of a cell layer or the like formed on a porous membrane can be monitored. For example, by measuring electrical characteristics such as a potential difference, a resistance, and a short circuit current using an electrode, a transport function of a fluid and an ion passed through a cell layer or the like formed on a porous membrane and formation of a barrier can be confirmed.

SUMMARY OF THE INVENTION

Incidentally, since a human body is complicated, only one measurement is not enough to accurately evaluate cells and the like using the channel device. That is, in order to perform accurate evaluation of cells and the like using the channel device, for example, it is preferable to perform a plurality of kinds of measurement at the same time, such as simultaneously performing of imaging of cells on the porous membrane and measurement of a resistance value using an electrode, and performing an evaluation based on a plurality of measurement results.

However, it is difficult for the channel device in the related art to perform a plurality of kinds of measurement at the same time, in particular, to perform optical measurement such as measurement using a fluorescent label and imaging of cells and electrical measurement using an electrode at the same time.

An object of the present invention is to solve the above problems of the related art, and is to provide a channel device used as an organ model or the like and capable of simultaneously performing optical measurement and electrical measurement.

In order to solve this problem, the present invention has the following configuration.

[1] A channel device comprising:
a first channel member having a first channel;
a second channel member having a second channel;
a porous membrane provided between the first channel member and the second channel member; and
a pair of transparent electrodes provided so as to interpose the first channel and the second channel therebetween.

[2] The channel device according to [1],
in which the pair of transparent electrodes is formed of the transparent electrode in contact with the first channel and the transparent electrode in contact with the second channel.

[3] The channel device according to [1] or [2],
in which at least one of the transparent electrodes is a planar electrode.

[4] The channel device according to [3],
in which at least one of the transparent electrodes is a planar electrode including the porous membrane in a case of being viewed from a direction orthogonal to a main surface of the first channel member.

[5] The channel device according to any one of [1] to [4],
in the transparent electrode is formed on an entire surface of the first channel member on which the first channel is formed.

[6] The channel device according to any one of [1] to [5],
in which the second channel member is a plate member having a through-hole that serves as the second channel,
a holding plate that abuts on the second channel member and closes the through-hole that serves as the second channel is further provided, and
the transparent electrode is formed on an entire surface of the holding plate that abuts on the second channel member.

[7] The channel device according to any one of [1] to [6],
in which the first channel member, or the first channel member and the second channel member are formed of a polymer material, and
the transparent electrode contains a carbon nanotube.

[8] The channel device according to [6],
in which the holding plate is formed of a polymer material, and the transparent electrode formed on the entire surface of the holding plate that abuts on the second channel member contains a carbon nanotube.

[9] The channel device according to any one of [1] to [8], in which the porous membrane has through-holes arranged in a honeycomb form.
[10] The channel device according to any one of [1] to [9], in which the porous membrane is formed of a polymer material.
[11] The channel device according to any one of [1] to [10], in which cells are fixed to the porous membrane.
[12] The channel device according to [11], in which the cells fixed to the porous membrane are cells different between one surface and the other surface of the porous membrane.

According to the channel device of an aspect of the present invention, it is possible to simultaneously perform optical measurement and electrical measurement.

DESCRIPTION OF THE PREFERRED EMBODIMENTS

Hereinafter, a cell culture unit of the present invention will be described in detail based on preferred embodiments shown in the accompanying drawings.

The embodiments described below exemplify an example of the present invention, and do not limit the scope of the present invention. In addition, in order to clarify the description of each component, the dimension of each component in the drawing is appropriately changed. Therefore, the scale in the drawing is different from the actual one.

<Channel Unit>

Figure 1:
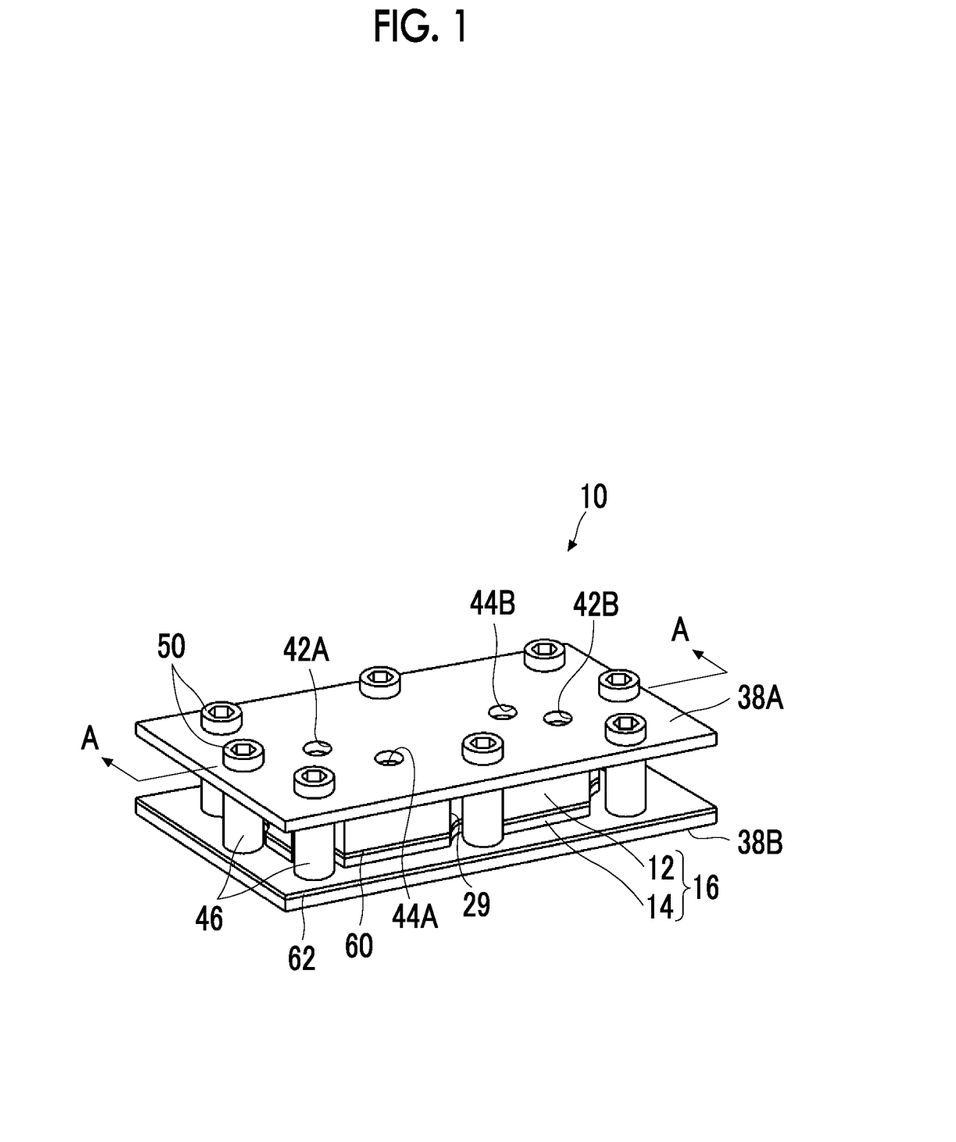
FIG. 1 is a schematic perspective view showing an overall structure of an example of a channel device of an aspect of the present invention.
Figure 2:
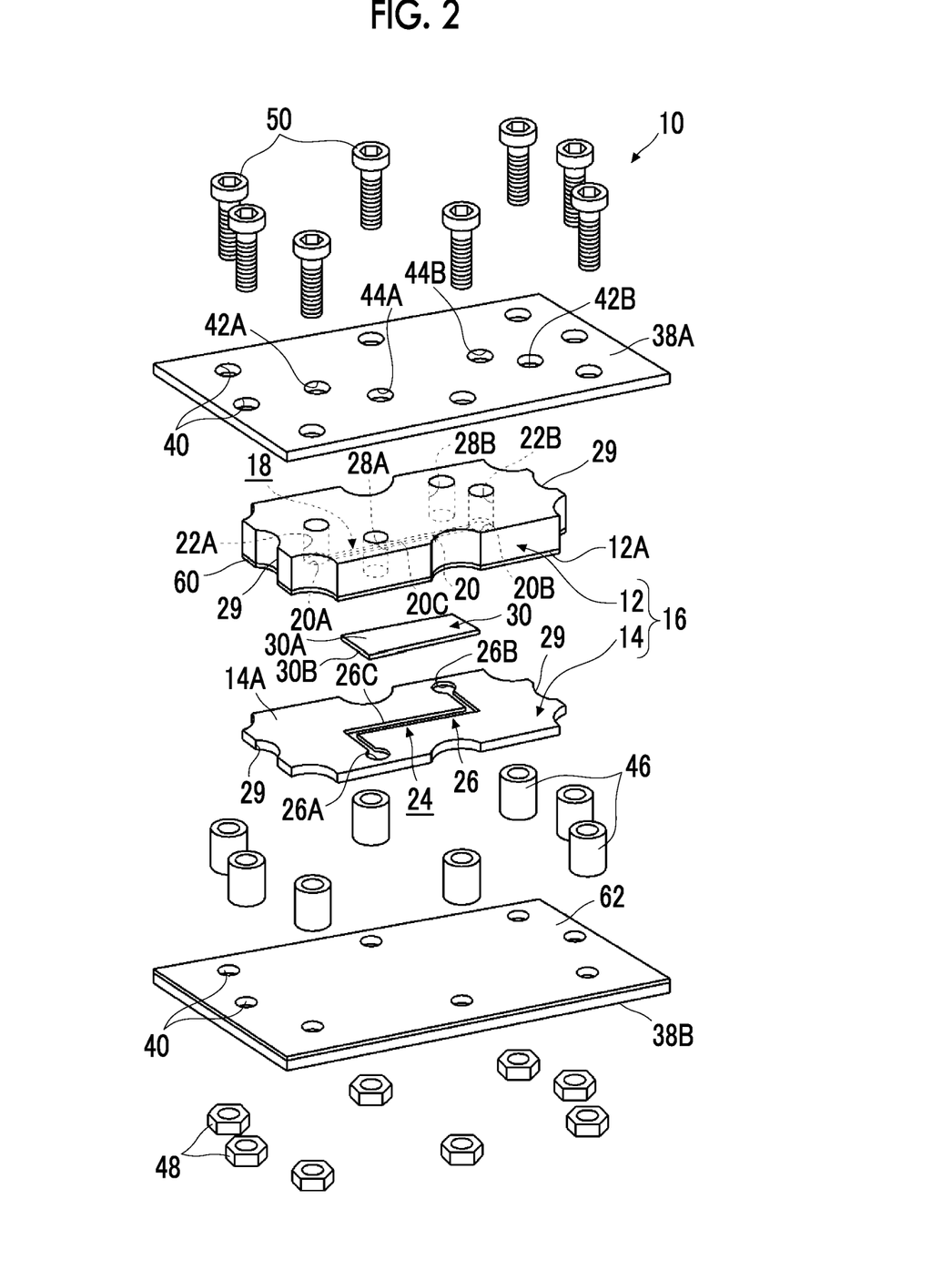
FIG. 2 is a schematic exploded perspective view showing the overall structure of the channel device shown in FIG. 1.

FIG. 1 is a schematic perspective view of an example of a channel device of an embodiment of the present invention, and FIG. 2 is a schematic exploded perspective view of the channel device shown in FIG. 1.

The illustrated example is merely one embodiment of the present invention, and the channel device of the embodiment of the present invention is not limited to this embodiment.

As shown in FIGS. 1 and 2, a channel device 10 has a channel unit 16 including a first channel member 12 and a second channel member 14 that are laminated in a thickness direction. In the following description, an upper side in FIGS. 1 and 2 is referred to as "upper" and a lower side in FIGS. 1 and 2 is referred to as "lower". The upper side in FIGS. 1 and 2 is the first channel member 12 side, and the lower side in FIGS. 1 and 2 is the second channel member 14 side.

A material of the first channel member 12 and the second channel member 14 is preferably, for example, an elastic transparent material such as polydimethylsiloxane (PDMS).

As the material forming the first channel member 12 and the second channel member 14, in addition to PDMS, a polymer material (resin material and polymer) such as an epoxy resin, a urethane resin, a styrenic thermoplastic elastomer, an olefinic thermoplastic elastomer, an acrylic thermoplastic elastomer, and a polyvinyl alcohol is used.

Here, a rubber hardness of the first channel member 12 and the second channel member 14 is preferably 20 to 80 degrees, and more preferably 50 to 70 degrees.

The "rubber hardness" can be evaluated by measuring a hardness of the first channel member 12 and the second channel member 14 with a type A durometer according to a method specified in JIS K6253:2012.

As shown in FIG. 2, on a lower surface of the first channel member 12, that is, on a surface 12A facing the second channel member 14, a recessed part 20 that defines a first channel 18 (first micro channel 18) is formed. The recessed part 20 has an inflow port 20A and an outflow port 20B, and a channel portion 20C that makes the inflow port 20A and the outflow port 20B communicate with each other. The first channel member 12 is formed with through-holes 22A and 22B that penetrate through the first channel member 12 in a thickness direction and whose lower ends communicate with the inflow port 20A and the outflow port 20B, respectively. A width and a depth of the first channel 18 (recessed part 20) may be appropriately set according to a size and application of the channel device 10.

In addition, as will be described later in detail, a first transparent electrode 60 is formed (excluding the through-holes) on the entire lower surface of the first channel member 12 including the recessed part 20 (first channel 18).

On the other hand, the second channel member 14 is formed with a through-hole 26 that penetrates through the second channel member 14 in a thickness direction and defines a second channel 24 (second micro channel 24). The second channel 24 is formed by providing a holding plate 38B, which will be described later, abutting on a lower surface of the second channel member 14 (surface opposite to the first channel member 12) to close a lower surface side of the through-hole 26. A width and a depth of the second channel 24 (through-hole 26) may be appropriately set according to a size and application of the channel device 10.

The through-hole 26 has an inflow port 26A and an outflow port 26B, and a channel portion 26C that makes the inflow port 26A and the outflow port 26B communicate with each other.

Here, the inflow port 26A and the outflow port 26B of the second channel member 14 are provided at positions that do not overlap the inflow port 20A and the outflow port 20B of the first channel member 12 in a planar view. On the other hand, the channel portion 26C of the second channel member 14 is provided at a position overlapping the channel portion 20C of the first channel member 12 in a planar view.

The planar view, in other words, refers to a case where the channel device 10 of the embodiment of the present invention is viewed from a direction orthogonal to a main surface of the first channel member 12. In addition, the main surface refers to a largest surface of a sheet-shaped material, a plate-shaped material, a film-shaped material, or the like.

The first channel member 12 is formed with through-holes 28A and 28B that penetrate through the first channel member 12 in a thickness direction and whose lower ends communicate with the inflow port 26A and the outflow port 26B of the second channel member 14.

Further, a recessed part 29 is provided on an outer peripheral surface (side surface) of the channel unit 16 (first channel member 12 and second channel member 14) at a position where a spacer 46 which will be described later is disposed.

<Porous Membrane>

A porous membrane 30 is disposed between facing surfaces 12A and 14A of the first channel member 12 and the second channel member 14. The porous membrane 30 is formed of, for example, a polymer material, and particularly preferably formed of a hydrophobic polymer material that can be dissolved in a hydrophobic organic solvent. The hydrophobic organic solvent is a liquid having a solubility in water at 25° C. of 10 (g/100 g water) or less.

Examples of the polymer material include polystyrene, polyacrylate, polymethacrylate, polyacrylamide, polymethacrylamide, polyvinyl chloride, polyvinylidene chloride, polyvinylidene fluoride, polyhexafluoropropene, polyvinyl ether, polyvinylcarbazole, polyvinyl acetate, polytetrafluoroethylene, polyester, polylactone, polyamide and polyimide, polyurethane, polyurea, polybutadiene, polycarbonate, polyaromatics, polysulfone, polyethersulfone, a polysiloxane derivative, and cellulose acylate.

Examples of polyester include polyethylene terephthalate, polyethylene naphthalate, polyethylene succinate, polybutylene succinate, polylactic acid, and poly-3-hydroxybutyrate. Examples of polylactone include polycaprolactone and the like. Examples of polyamide and polyimide include nylon and polyamic acid. Examples of cellulose acylate include triacetyl cellulose, cellulose acetate propionate, and cellulose acetate butyrate.

These polymer materials may be homopolymers, copolymers, polymer blends, polymer alloys, and the like, as necessary, from a viewpoint of a solubility in a solvent, an optical property, an electrical property, a film hardness, an elasticity, or the like. In addition, these polymer materials may be used alone or in combination of two or more. A material of the porous membrane 30 is not limited to the polymer material, and various materials can be selected from a viewpoint of cell adhesiveness.

An upper surface 30A and a lower surface 30B of the porous membrane 30 have a size that substantially covers the channel portions 20C and 26C of the first channel 18 and the second channel 24.

The porous membrane 30 is provided so as to cover the first channel 18 and the second channel 24. Thereby, the porous membrane 30 separates the first channel 18 and the second channel 24 from each other.

Specifically, the upper surface 30A of the porous membrane 30, that is, a main surface facing the first channel member 12 defines the first channel 18 together with the recessed part 20 of the first channel member 12.

The lower surface 30B of the porous member 30, that is, a main surface facing the second channel member 14 defines the second channel 24 together with the through-hole 26 of the second channel member 14.

Figure 3:
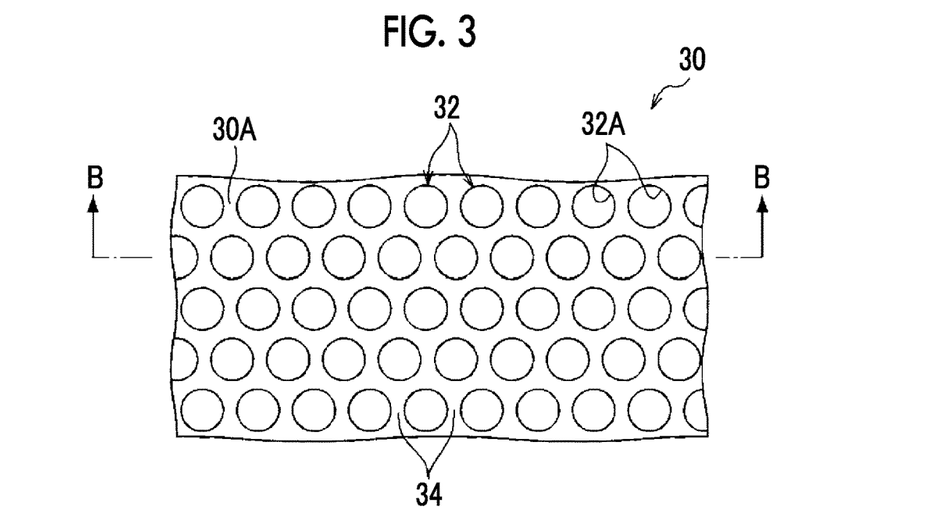
FIG. 3 is a schematic plan view showing an example of a porous membrane of the channel device shown in FIG. 1.
Figure 4:
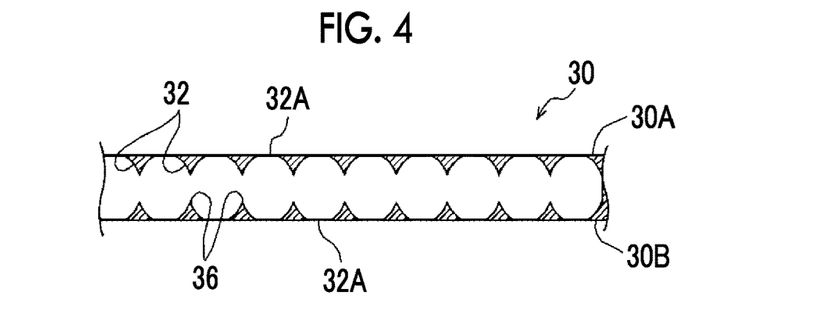
FIG. 4 is a schematic cross-sectional view taken along the line B-B of FIG. 3.

As shown in FIGS. 3 and 4, a plurality of through-holes 32 that penetrate through the porous membrane 30 in a thickness direction are formed in the porous membrane 30, and openings 32A of the through-holes 32 are provided on the upper surface 30A and the lower surface 30B of the porous membrane 30. As shown in FIG. 3, the opening 32A has a circular shape in a planar view. The openings 32A are provided to be spaced from each other, and a flat portion 34 extends between the openings 32A adjacent to each other. The opening 32A is not limited to a circular shape, and may have a polygonal shape, an elliptical shape, an irregular shape, or the like.

A plurality of the openings 32A are regularly arranged. In the present invention, as an example, the openings 32A are arranged in a honeycomb form.

The arrangement in a honeycomb form is an arrangement in which a parallel hexagon or a shape close to this is taken as a unit and centers of the openings 32A are located at vertices and an intersection of diagonal lines of these figures. The parallel hexagon is preferably a regular hexagon.

Here, the "center of the opening" means the center of the opening 32A in a planar view.

The arrangement of the openings 32A is not limited to the honeycomb form, and may be a lattice form or a face-centered lattice form. The arrangement in a lattice form is an arrangement in which a parallelogram or a shape close to this is taken as a unit and the centers of the openings are located at vertices of these figures. The arrangement in a face-centered lattice form is an arrangement in which a parallelogram or a shape close to this is taken as a unit and the centers of the openings are located at vertices and an intersection of diagonal lines of these figures. In the above description, the parallelogram includes a square, a rectangle, and a rhombus, and a square is preferable.

It is preferable that the openings 32A be arranged in a honeycomb form in order to easily achieve the following opening ratio.

In the porous membrane 30, a variation coefficient of an opening diameter of the opening 32A is preferably 10% or less, and the smaller the better. The smaller the variation coefficient of the opening diameter, the more uniformly red blood cells and the like can pass through the plurality of through-holes 32 of the porous membrane 30.

In addition, an opening ratio (void volume) of the porous membrane 30 is preferably 50% or more. By setting the opening ratio to 50% or more, it is possible to prevent the movement of red blood cells and the like from being blocked by the porous membrane 30. In a case where the void volume is too large, a strength of the porous membrane 30 is insufficient with respect to a required strength, and thus the void volume is preferably 95% or less.

Here, the "opening ratio" refers to a ratio of V2 to V1 in percentage in a case where V1 is a unit volume of the porous membrane 30 in a case where it is assumed that a main surface of the porous membrane 30 is smooth, that is, there is no opening 32A, V2 is a sum of volumes of the through-hole 32 and a communication hole 36 provided per unit volume, and units of V1 and V2 are the same.

As shown in FIG. 4, the through-hole 32 of the porous membrane 30 has a spherical trapezoidal shape in which an upper end and a lower end of a sphere are cut off. The through-holes 32 adjacent to each other communicate with each other by the communication hole 36 inside the porous membrane 30.

It is preferable that one through-hole 32 communicate with all adjacent through-holes 32. As in the present invention, in a case where the openings 32A of the plurality of through-holes 32 are arranged in a honeycomb form, it is preferable that one through-hole 32 communicate with six adjacent through-holes 32 by six communication holes 36, respectively.

The through-hole 32 may have a barrel shape, a columnar shape, a polygonal column shape, or the like, and the communication hole 36 may be a cylindrical void that connects the adjacent through-holes 32 to each other.

Examples of a method of manufacturing the porous membrane 30 having the through-holes 32 include a nano-printing method, a condensation method, an etching method, a sandblasting method, and a press molding method.

The nano-printing method is a method of manufacturing the through-holes 32 by pouring a material forming the porous membrane 30 into a mold having an uneven shape or pressing the mold against the material forming the porous membrane 30. The condensation method is a method in which a surface of the material forming the porous membrane 30 is condensed to form the through-holes 32 using a water droplet as a mold.

As compared with the other methods, in the condensation method, a film thickness of the porous membrane 30 can be reduced, a void volume and an opening ratio of the opening 32A can be increased, and the communication hole 36 can be provided in the porous membrane 30. Therefore, in the present invention, the porous membrane 30 is manufactured by the condensation method.

Details of the condensation method are described in, for example, JP4945281B, JP5422230B, JP2011-074140A, and JP5405374B.

In the channel device 10 of the embodiment of the present invention, the porous membrane is not limited to those having such through-holes, and various kinds of known porous membranes (porous materials) such as non-woven fabrics and membranes having three-dimensional voids can be used.

In the channel device 10 of the embodiment of the present invention, it is preferable that at least a region where cells are seeded on the main surface of the porous membrane 30 be coated with at least one selected from the group consisting of fibronectin, collagen, laminin, vitronectin, gelatin, perlecan, nidogen, proteoglycan, osteopontin, tenascin, nephronectin, basement membrane matrix, and polylysine. Examples of collagen include type I collagen, type IV collagen, and type V collagen.

By coating the porous membrane 30 with these materials, it is possible to enhance cell adhesiveness.

In a case where the channel device 10 of the embodiment of the present invention is used as an organ simulator (organ model) or the like, the main surface of the porous membrane 30 may have a cell layer that constitutes an organ to be simulated.

The main surface of the porous membrane 30 have the cell layer, whereby the inside of the first channel 18 and the inside of the second channel 24 can be made to have an environment close to the inside of the organ to be simulated.

That is, the channel device of the embodiment of the present invention may be a cell culture device for culturing cells, or may be a channel device for measurement that has a cell layer and performs measurement for evaluating cells and/or drug solutions.

Examples of the cells provided on the main surface of the porous membrane 30 include parenchymal cells, stromal cells, muscle cells, fibroblasts, nerve cells, endothelial cells, epithelial cells, and cells that differentiate into any of these.

Examples of the parenchymal cells include hepatic parenchymal cells and pancreatic parenchymal cells. Examples of the stromal cells include pericytes. Examples of the muscle cells include smooth muscle cells, cardiomyocytes, and skeletal muscle cells. Examples of the endothelial cells include vascular endothelial cells and lymphatic endothelial cells. Examples of the epithelial cells include alveolar epithelial cells, oral epithelial cells, bile duct epithelial cells, intestinal epithelial cells, pancreatic duct epithelial cells, renal epithelial cells, renal tubular epithelial cells, and placental epithelial cells. Examples of the cells that differentiate into any of these include progenitor cells, mesenchymal stem cells, and pluripotent stem cells.

Examples of the pluripotent stem cells include embryonic stem cells (ES cells), induced pluripotent stem cells (iPS cells), embryonic germ cells (EG cells), embryonal carcinoma cells (EC cells), multipotent adult progenitor cells (MAP cells), adult pluripotent stem cells (APS cells), and multi-lineage differentiating stress enduring cells (Muse cells).

As cells, cells having gene mutation and/or cells derived from a patient may be used for the purpose of reproducing a pathological condition.

The cell layer provided on the main surface of the porous membrane 30 may have the same cell layer on both surfaces, or may have cell layers different from each other on each surface.

As an example, a vascular endothelial cell layer is provided on one surface of the porous membrane 30 and a smooth muscle cell layer is provided on the other surface of the porous membrane 30, whereby the channel device 10 serving as a vascular wall model can be obtained.

<Holding Plate>

As shown in FIGS. 1 and 2, the channel device 10 has a holding plate 38A on the upper side (first channel member 12 side) and a holding plate 38B on the lower side (second channel member 14 side) as a holding member that holds the channel unit 16 in a compressed state in a thickness direction.

The holding plate 38A and the holding plate 38B are provided separately from the channel unit 16 at both ends of the channel unit 16 in a thickness direction, that is, on the upper side of the first channel member 12 and the lower side of the second channel member 14, and have a size that covers the entire upper surface of the first channel member 12 and the entire lower surface of the second channel member 14.

Both the holding plate 38A and the holding plate 38B are preferably formed of a rigid and transparent polymer material.

Accordingly, examples of a constituent material of the holding plate 38A and the holding plate 38B include cycloolefin polymer, acrylic, polycarbonate, polystyrene, and polyethylene terephthalate. In addition, the holding plate 38A and the holding plate 38B are preferably harder than the first channel member 12 and the second channel member 14 described above, and further, a rubber hardness is preferably 80 degrees or more, and more preferably 90 degrees or more.

As shown in FIG. 2, a plurality of bolt holes 40 penetrating in a thickness direction are formed at positions corresponding to each other on the holding plate 38A and the holding plate 38B. The number of bolt holes 40 is eight in the illustrated example. The holding plate 38A provided on the upper side of the first channel member 12 has through-holes 42A, 42B, 44A, and 44B that communicate with the through-holes 22A, 22B, 28A, and 28B of the first channel member 12, respectively.

Tubes (not shown) are connected to the through-holes 42A, 42B, 44A, and 44B, respectively, and a solution, a cell suspension, or the like flows into the first channel 18 and the second channel 24 through the tubes, and the solution, the cell suspension, or the like flows out from the first channel 18 and the second channel 24.

A plurality of the spacers 46 that define intervals between the holding plates 38 are provided outside the recessed part 29 of the channel unit 16 between a pair of the holding plates 38. The number of spacers 46 is eight in the illustrated example. The spacers 46 are cylindrical members having an inner diameter substantially the same as an inner diameter of the bolt hole 40, and are disposed at positions corresponding to the bolt holes 40, respectively.

Figure 5:
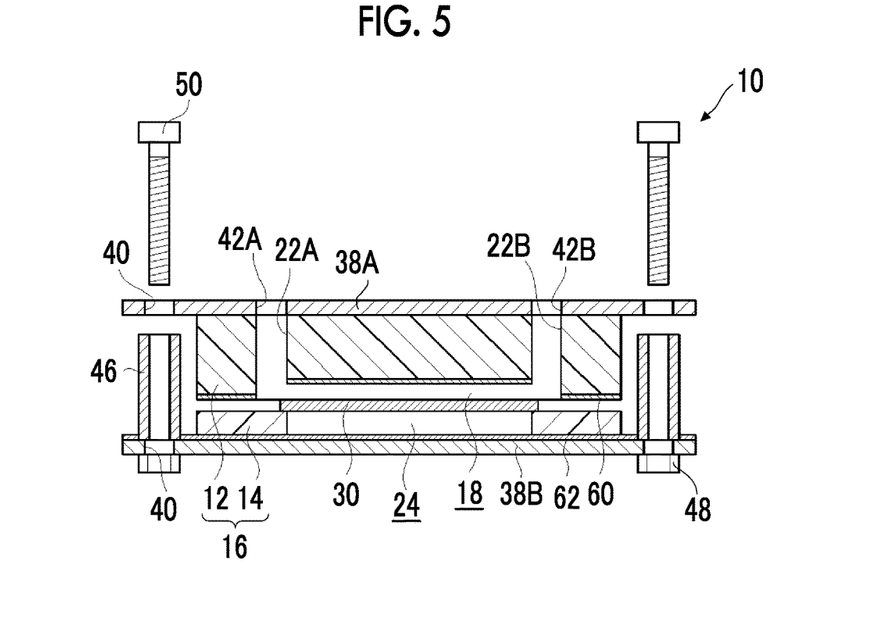
FIG. 5 is a schematic cross-sectional view which is taken along the line A-A in FIG. 1 and shows the channel device before a channel unit is fixed.
Figure 6:
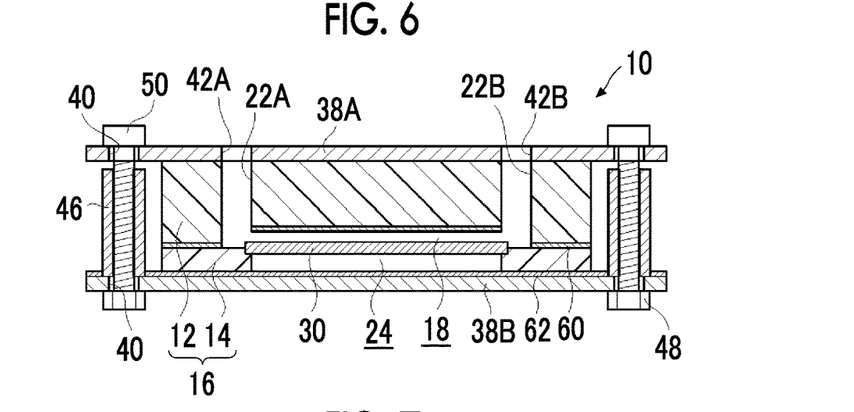
FIG. 6 is a schematic cross-sectional view which is taken along the line A-A in FIG. 1 and shows the channel device after the channel unit is fixed.

As shown in FIGS. 5 and 6, the pair of holding plates 38 are joined to each other by a plurality of bolts 50 that are inserted through the bolt holes 40 and the spacers 46 and fixed by nuts 48. In this case, the first channel member 12 and the second channel member 14 are compressed and held by the pair of holding plates 38 with the porous membrane 30 interposed therebetween.

<Transparent Electrode>

In the channel device 10 of the embodiment of the present invention, a second transparent electrode 62 is disposed on the holding plate 38B that abuts on the second channel 24 so as to cover an entire surface abutting on the second channel member 14. As described above, the second channel 24 is formed by the holding plate 38B abutting on the lower surface of the second channel member 14 and closing the lower surface of the through-hole 26. Accordingly, the lower surface side of the second channel 24 is the second transparent electrode 62, that is, the second transparent electrode 62 is in contact with the second channel 24.

As described above, the lower surface of the first channel member 12 has the recessed part 20 that defines the first channel 18. The first transparent electrode 60 is provided on the lower surface of the first channel member 12 so as to cover the entire surface including the recessed part 20. That is, the first transparent electrode 60 is in contact with the first channel 18.

In the channel device 10, a pair of transparent electrodes (electrode pair) is configured by the first transparent electrode 60 in contact with the first channel 18 and the second transparent electrode 62 in contact with the second channel 24.

The channel device 10 of the embodiment of the present invention has the first transparent electrode 60 and the second transparent electrode 62 as described above, so that optical measurement and electrical measurement can be performed at the same time.

As described above, since a human body is complicated, only one type of measurement is not enough to accurately evaluate cells and the like using the channel device, and it is preferable to perform so-called multi-validation in which a plurality of types of measurements are performed at the same time.

Figure 7:
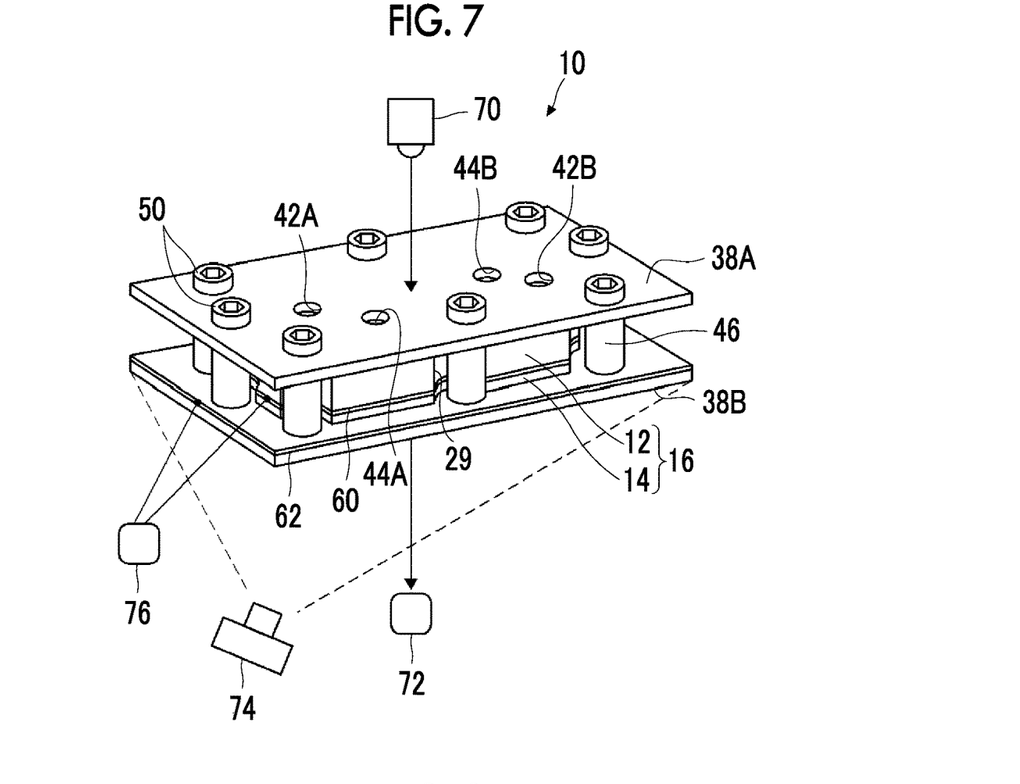
FIG. 7 is a view conceptually showing an example of a measuring method using the channel device shown in FIG. 1.

As an example of the measurement using the channel device, as shown conceptually in FIG. 7, evaluation of permeability of a membrane in which a fluorescently labeled large molecule is caused to flow through the first flow channel 18 or the second flow channel 24, excitation light is emitted from a light source 70, and fluorescence is measured by an optical sensor 72 is exemplified.

In addition, by causing a liquid to flow through the first channel 18 and/or the second channel 24 and imaging (visualizing) the cell layer or the like formed on the porous membrane 30 using an imaging camera 74 such as a transmission electron microscope and a fluorescence microscope, a structure of the cell layer or the like can be evaluated.

Furthermore, by connecting an electric sensor 76 to the first transparent electrode 60 and the second transparent electrode 62 and measuring electrical characteristics such as a potential difference, a resistance, and a short circuit current, a transport function of a fluid and an ion passed through a membrane and formation of a barrier can be evaluated.

However, in the channel device in the related art, in a case where electrodes are formed corresponding to a first channel and a second channel in order to measure electrical characteristics of a cell layer and the like formed on a porous membrane, the electrodes are usually formed of a metal, and thus the electrodes act as a like-shielding member, and optical measurement and evaluation such as fluorescence measurement and imaging of the cell layer cannot be properly performed.

Therefore, the channel device in the related art cannot perform an electrical measurement and an optical measurement at the same time.

With respect to this, in the channel device 10 of the embodiment of the present invention, a pair of the first transparent electrode 60 and the second transparent electrode 62 is provided so as to interpose the first channel 18 and the second channel 24 therebetween.

In the channel device 10 of the embodiment of the present invention, even though the pair of electrodes is provided so as to interpose the first channel 18 and the second channel 24 therebetween, the electrodes are transparent electrodes, and thus the electrodes do not interfere with optical measurement methods such as fluorescence measurement and imaging of the cell layer. Therefore, according to the channel device 10 of the embodiment of the present invention, electrical measurement and optical measurement such as fluorescence measurement using the light source 70 and the optical sensor 72 as shown in FIG. 7, imaging of the cell layer using the imaging camera 74, and resistance measurement using the electric sensor 76 can be performed at the same time.

In addition, since the transparent electrode is used, even though the electrode is a planar electrode, it does not interfere with optical measurement. Therefore, stable electrical measurement can be performed with an electrode having a sufficient area. Furthermore, it is also possible to extract an electrical property of the surface of the cell layer formed on the porous membrane 30 as an electrical signal.

In the channel device 10 of the embodiment of the present invention, the first transparent electrode 60 and the second transparent electrode 62 are transparent electrodes having conductivity.

In the present invention, the term "having conductivity" means that a sheet resistance value is 0.1 to 10,000Ω/□ (Ohms per Square (Ω/sq)), and includes what is generally called an electric resistance layer. In a general-purpose power source is used, a lower sheet resistance value is preferable, specifically, 300Ω/□ or less is preferable, 200Ω/□ or less is more preferable, and 100Ω/□ or less is still more preferable. In the present invention, a sheet resistance value (surface resistivity) may be measured according to Japanese Industrial Standards (JIS) K 7194.

In addition, in the present invention, the term "transparent" means that a transmittance is 60% to 99.99%. A transmittance of the transparent electrode is preferably 75% or more, more preferably 80% or more, and still more preferably 90% or more. In the present invention, for a transmittance, a total light transmittance [%] may be measured according to JIS K 7361-1.

In the channel device 10 of the embodiment of the present invention, materials of the first transparent electrode 60 and the second transparent electrode 62 are not limited, and various materials used as transparent electrodes in various electronic devices (electronic devices, electronic elements) can be used.

Specifically, examples of the materials included in the first transparent electrode 60 and the second transparent electrode 62 include a metal oxide, a carbon nanotube, graphene, a polymer conductor, a metal nanowire, and a metal mesh. Examples of the metal oxide include indium tin oxide (ITO) and the like. Examples of the carbon nanotube include a carbon nanotube (CNT) and a carbon nanobud (CNB). Examples of the polymer conductor include polyacetylene, polypyrrole, polyphenol, polyaniline, and polyethylenedioxythiophene/polystyrene sulfonic acid (PEDOT/PSS). Examples of the metal nanowire include a silver nanowire and a copper nanowire. Examples of the metal mesh include a silver mesh and a copper mesh.

A transparent electrode having the metal mesh is preferably formed of a conductive fine particle such as silver and copper dispersed in a matrix, rather than a transparent electrode formed of only a metal, from a viewpoint of a heat shrinkage rate.

A transparent electrode formed of these materials may be formed by a known method according to the material.

For example, in a case of a transparent electrode containing a carbon nanotube, the transparent electrode may be formed by a coating method in which a coating material in which a carbon nanotube is dispersed is prepared, the prepared coating material is applied to a portion where the transparent electrode is to be formed such as the lower surface of the first channel member 12 and dried, and further heat-treated as necessary.

In a case of a transparent electrode containing a carbon nanobud, similarly, the transparent electrode may be formed on a portion where the transparent electrode is to be formed such as the lower surface of the first channel member 12 by a direct dry printing (DDP) method described on 1012 page of society for information display (SID) 2015 DIGEST.

Furthermore, in a case of a transparent electrode containing a silver nanowire, similarly, the transparent electrode may be formed on a portion where the transparent electrode is to be formed such as the lower surface of the first channel member 12 by a method described in Example 1 of US2013/0341074A.

Here, in the channel device 10 of the embodiment of the present invention, both the first channel member 12 on which the first transparent electrode 60 is formed and the holding plate 38B on which the second transparent electrode 62 is formed are preferably formed of a polymer material.

In consideration of this point, the material forming the first transparent electrode 60 and the second transparent electrode 62 is preferably a material that can be formed by the coating method rather than a vapor phase film-forming method (vapor phase depositing method) such as plasma chemical vapor deposition (CVD), sputtering, and vacuum deposition. Among them, a carbon nanotube is preferably exemplified. In addition, in the channel device 10 of the embodiment of the present invention, as described above, observation of fluorescence and the like is also available, but among metal materials such as metal oxides, there is a material that emits light by absorbing excitation light and/or fluorescence. Also in this point, a carbon nanotube that does not absorb excitation light and/or fluorescence is preferable as the material of the transparent electrode.

As will be described later, in the channel device of the embodiment of the present invention, the transparent electrode is not limited to the configuration in which the transparent electrode is formed on the entire lower surface of the first channel member 12 and the entire surface of the holding plate 38B as in the present invention.

Various shapes and sizes of the transparent electrode are available. Accordingly, the transparent electrode may be linear or planar, but for reasons described above, it is preferable that at least one transparent electrode, preferably both transparent electrodes, be a planar electrode. This allows a stable electrical measurement with an electrode having a sufficient area.

In the present invention, the planar electrode refers to an electrode having an area larger than an area of a region where the first channel 18 and the second channel 24 are separated from each other by the porous membrane 30.

It is preferable that at least one transparent electrode, preferably both transparent electrodes, have a shape and a size that include the porous membrane 30 in a case of being viewed from a direction orthogonal to the main surface of the first channel member 12. A case of being viewed from a direction orthogonal to the main surface of the first channel member 12 is the same as the above-described planar view. In particular, it is preferable that the transparent electrode, such as the first transparent electrode 60, which abuts on the porous membrane 30 have such a configuration, so that it is possible to extract the electrical property of the surface of the cell layer or the like formed on the porous membrane 30.

<Method of Manufacturing Channel Device>

Figure 8:
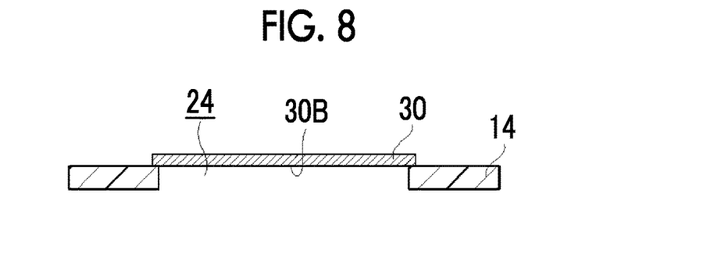
FIG. 8 is a schematic cross-sectional view showing a manufacturing process of the channel device shown in FIG. 1.

In a case where the channel device 10 of embodiment of the present invention is manufactured, first, the porous manufacturing 30 having the main surface attached with a sterilized paper is prepared. Then, a sterilized paper on the lower surface 30B of the porous membrane 30 is peeled off by tweezers, and as shown in FIG. 8, the porous membrane 30 is placed on the second channel member 14 in which the through-hole 26 is formed and the porous membrane 30 and the second channel member 14 are joined to each other.

Figure 9:
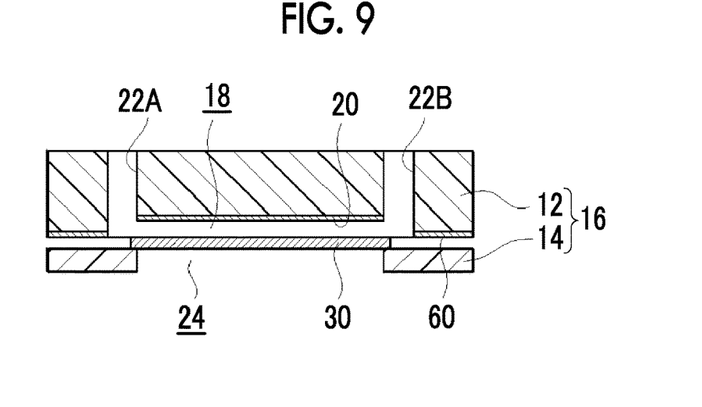
FIG. 9 is a schematic cross-sectional view showing a manufacturing process of the channel device shown in FIG. 1.

Next, a sterilized paper on the upper surface 30A of the porous membrane 30 is peeled off by tweezers, the position of the second channel member 14 is aligned with the position of the first channel member 12 on which the first channel member 60 is formed while being checked with a microscope, and as shown in FIG. 9, the first channel member 12 in which the recessed part 20 is formed is laminated on the porous membrane 30. Thereby, the first channel 18 is defined by the recessed part 20 of the first channel member 12 and the porous membrane 30. The first channel 18 is in contact with the first transparent electrode 60 formed on the first channel member 12.

Figure 10:
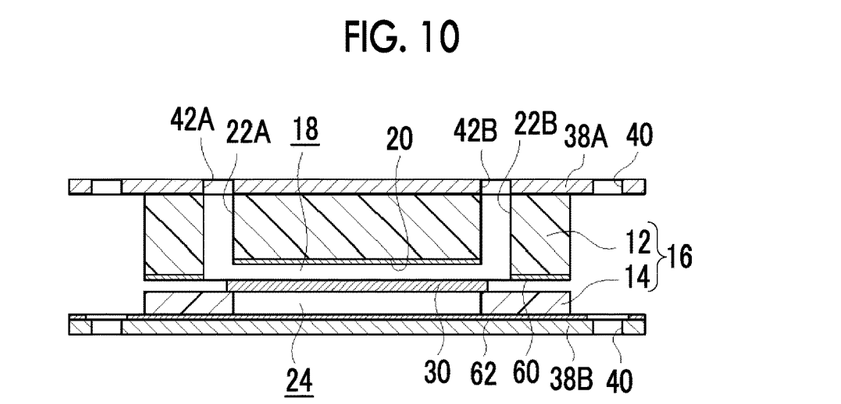
FIG. 10 is a schematic cross-sectional view showing a manufacturing process of the channel device shown in FIG. 1.

Next, as shown in FIG. 10, the holding plate 38A is placed on the upper surface of the first channel member 12 while aligning the positions of the through-holes 22A and 22B with the positions of the through-holes 42A and 42B, respectively.

After that, the channel unit 16 is turned over, and the holding plate 38B on which the second transparent electrode 62 is formed is placed on the lower surface of the second channel member 14. Thereby, the second channel 24 is defined by the through-hole 26 of the second channel member 14, the porous membrane 30, and the holding plate 38B. The second channel 24 is in contact with the second transparent electrode 62 formed on the holding plate 38B.

Figure 11:
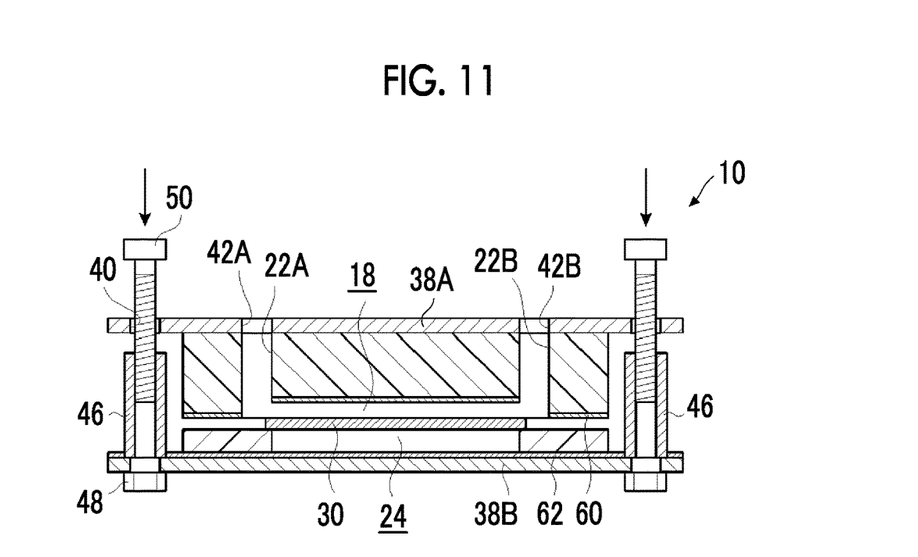
FIG. 11 is a schematic cross-sectional view showing a manufacturing process of the channel device shown in FIG. 1.

Finally, as shown in FIG. 11, the spacer 46 is disposed around the channel unit 16, and the holding plate 38A and the holding plate 38B are fastened by the bolts 50 and the nuts 48, whereby the channel device 10 is manufactured.

Note that the above manufacturing process is an example, and the order may be changed. In addition, another process may be added to the above-mentioned process.

Other Embodiments

Although one embodiment of the channel device of the embodiment of the present invention has been described above, the present invention is not limited to this embodiment and can be variously modified and implemented in addition to the above-described configuration without departing from the spirit of the present invention.

For example, the transparent electrode corresponding to the first channel 18 may be disposed only on the entire wall surface of the first channel 18 (recessed part 20), or may be disposed only on the upper surface of the first channel 18, or may be disposed only on the side surface of the first channel 18, instead of the entire lower surface of the first channel member 12 including the recessed part 20.

Similarly, the transparent electrode corresponding to the second channel 24 may be disposed only on the portion of the holding plate 38B corresponding to the second channel 24, or may be disposed only on the side surface of the second channel 24 (through-hole 26), instead of the entire surface of the holding plate 38B.

In the present invention, the transparent electrode may not be in contact with the first channel 18 and the second channel 24.

For example, at least one of the transparent electrode corresponding to the first channel 18 or the transparent electrode corresponding to the second channel 24 may be disposed to be spaced from the channel, for example, by disposing the transparent electrode corresponding to the first channel 18 on the upper surface of the first channel member 12, that is, the surface opposite to the porous membrane 30, and disposing the transparent electrode corresponding to the second channel 24 on the lower surface of the holding plate 38B, that is, the surface opposite to the porous membrane 30.

By providing the transparent electrode to be spaced from the first channel 18 and/or the second channel 24, it is possible to measure an impedance and a dielectric constant.

That is, in the channel device of the embodiment of the present invention, the pair of transparent electrodes can be disposed at various positions and in various shapes as long as it is provided so as to interpose the first channel 18 and the second channel 24 (at least a part thereof) therebetween.

Furthermore, the channel device 10 of the embodiment of the present invention has the configuration in which the porous membrane 30 is disposed between the first channel member 12 and the second channel member 14, and this laminate is interposed between the holding plate 38A and the holding plate 38B. However, the present invention is not limited to this configuration.

For example, by using a second channel member having a recessed part having a bottom without using a holding plate and instead of the through-hole 26 that defines the second channel 24, as in a channel device (an organomimetic device having a micro channel) disclosed in JP2011-528232A, the channel device may be configured by a first channel member, a porous membrane, and the second channel member.

In addition, by using a first channel member having a through-hole that defines a first channel instead of a recessed part that defines a first channel as the first channel member, the through-hole may be closed by a holding plate. In this case, the transparent electrode corresponding to the first channel may be provided on the lower surface (the surface on the porous membrane side) of the first channel member or on the main surface of the holding plate.

Although the channel device of the embodiment of the present invention has been described above in detail, the present invention is not limited to the above-mentioned examples, and various improvements and changes may be made without departing from the scope of the present invention.

EXAMPLES

Hereinafter, the features of the present invention will be described more specifically with reference to examples. However, the scope of the present invention should not be construed as being limited by specific examples described below.

<Manufacturing of Channel Device>

The channel device 10 as shown in FIG. 1 was manufactured by the method described above.

The first channel member 12 and the second channel member 14 were made of PDMS, and the holding plates 38A and 38B were made of a cycloolefin polymer. Both the first channel 18 (recessed part 20) and the second channel 24 (through-hole 26) were set to have a width of 300 μm and a depth of 300 μm.

The first transparent electrode 60 and the second transparent electrode 62 that contain a carbon nanotube and have a thickness of 0.5 μm were formed on the lower surface of the first channel member 12 (the surface on which the recessed part 20 is formed) and the upper surface of the holding plate 38B (the surface to be the first channel member 12 side) by a coating method. The same transparent electrode was manufactured and confirmed by the above-described method, and as a result, both the first transparent electrode 60 and the second transparent electrode 62 had a sheet resistance value of 300Ω/□ or less and a transmittance of 80% or more.

As the porous membrane 30, a polycarbonate film having the through-holes 32 arranged in a honeycomb form was prepared. The surface of the porous membrane 30 was covered with collagen. Thereafter, the porous membrane 30 was interposed between sterilized papers.

The sterilized paper on one surface of the porous membrane 30 was peeled off by tweezers. Next, the porous membrane 30 was set on the second channel member 14 with the surface from which the sterilized paper was peeled off facing downward (see FIG. 8).

Furthermore, ethanol was immersed in the porous membrane 30 by using a cotton swab to join the porous membrane 30 and the second channel member 14 to each other.

The sterilized paper on the other surface of the porous membrane 30 was peeled off by tweezers. Next, the first channel member 12 was aligned with the second channel member 14, and the first channel member 12 was laminated on the porous membrane 30 (see FIG. 9).

Next, the positions of the through-hole 22A and the through-hole 22B were aligned with the positions of the through-hole 42A and the through-hole 42B, respectively, and the holding plate 38A was placed on the upper surface of the first channel member 12. Furthermore, the laminated was turned over and the holding plate 38B was disposed on the lower surface of the second channel member 14 (see FIG. 10).

Furthermore, the spacer 46 is disposed around the channel unit 16, and the holding plate 38A and the holding plate 38B are fastened by the bolts 50 and the nuts 48, whereby the channel device 10 was manufactured (see FIG. 11).

<Cell Culture in Channel Device>

A suspension ($3 \times 10^{-6}$ cells/mL (liter)) of bone marrow-derived mesenchymal stem cells (manufactured by Lonza) was prepared. 200 µL of the prepared suspension was injected into the second channel 24 of the channel device 10.

The channel device 10 was inverted and left in a $CO_2$ incubator at 37° C. for 3 hours, and then a medium was caused to flow at a rate of 0.7 µL/min and cultured overnight.

Next, a suspension ($1 \times 10^{-6}$ cells/mL) of iPS cell-derived vascular endothelial cells (iCell EC manufactured by Corporate Directions Inc.) stained with CellTracker Orange (manufactured by Thermo Fisher Scientific Inc.) was prepared.

200 µL of the prepared suspension was injected into the first channel 18 of the channel device 10.

<Measurement of Cell>

Using an inverted fluorescence microscope (IX83 manufactured by Olympus Corporation), distribution of the iPS cell-derived vascular endothelial cells injected into the first channel 18 was observed.

Next, a fluorescently labeled dextran (D1830 manufactured by Thermo Fisher Scientific Inc.) was injected into the first channel 18, distribution of the fluorescently labeled dextran injected into the first channel 18 was observed using an inverted fluorescence microscope, and leakage of the fluorescently labeled dextran into the second channel 24 was evaluated.

At the same time, using a photodetector (photomultiplier tube H11902-20 manufactured by Hamamatsu Photonics K.K.), the amount of light transmitted through the second channel 24 was detected, and the amount of fluorescently labeled dextran leaking into the second channel 24 was measured.

Next, Phenol Red (manufactured by Tokyo Chemical Industry Co., Ltd.) was injected into the first channel 18, using a photodetector (Large-Area Balanced Photodetector PDB210A/M manufactured by Thorlabs Japan Inc.), the amount of light transmitted through the second channel 24 was detected, and the amount of Phenol Red leaking into the second channel 24 was measured. In this case, the fluorescently labeled dextran and Phenol Red have different molecular weights, and thus, in a case where there is a defect in a cell structure, a size of the defect can be quantitatively evaluated by comparing the amounts of leakage of each.

Using optical coherence tomography (OCT, refer to JP6184905B), a three-dimensional structure of cells in the first channel 18 and the second channel 24, the configuration of the cell layer, and the thickness of the cell layer were measured.

At the same time, a state of an internal structure was monitored by attaching wiring to the first transparent electrode 60 formed on the first channel 18 and the second transparent electrode 62 formed on the holding plate 38B and measuring the electric resistance inside the first channel 18 and the second channel 24 (digital multimeter DT4282 manufactured by HIOKI E.E. Corporation). A high electric resistance value indicates that the cells are densely disposed, a low electric resistance value indicates that a gap occurs between the cells, and a state of a cell structure can be quantitatively evaluated by the electric resistance value.

As described above, by performing multi-validation in which optical observation with an inverted fluorescence microscope, photodetection of a plurality of tracers, OCT, and electrical measurement are combined using the channel device of the embodiment of the present invention, it is possible to evaluate the cell structure and the defect size in a non-destructive and non-invasive manner.

With respect to this, in any one of these types of measurement, it is difficult to distinguish between the original "crevice" and "defect" of the defect structure and to quantify the size of each. The defect is an abnormal portion in which cells cannot properly exist.

That is, the channel device of the embodiment of the present invention is very effective for analysis of an organ model (biochip) by multi-validation.

It can be suitably used in various fields such as life science research, drug discovery, drug development and safety tests, and chemical and biological assays.

EXPLANATION OF REFERENCES

10: channel device
12: first channel member
12A, 14A: facing surface
14: second channel member
16: channel unit
18: first channel
20: recessed part
20A, 26A: inflow port
20B, 26B: outflow port
20C, 26C: channel portion
22A, 22B, 28A, 28B: through-hole
24: second channel
26: through-hole
29: recessed part
30: porous membrane
30A: upper surface
30B: lower surface
32: through-hole
32A: opening
34: flat portion
36: communication holes
38A, 38B: holding plate
40: bolt hole
42A, 42B, 44A, 44B: through-hole
46: spacer
48: nut
50: volt
60: first transparent electrode
62: second transparent electrode
70: light source
72: optical sensor
74: imaging camera
76: electric sensor

What is claimed is:
1. A channel device comprising:
a first channel member having a first channel;
a second channel member having a second channel;
a porous membrane provided between the first channel member and the second channel member to cover and separate between the first channel and the second channel;

a first transparent electrode provided in contact with the first channel and facing the porous membrane; and a second transparent electrode provided in contact with the second channel and facing the porous membrane, wherein the first channel is formed between the first channel member and the porous membrane, wherein the second channel is formed between the second transparent electrode, the second channel member and the porous membrane, wherein at least one of the first transparent electrode and the second transparent electrode is a planar electrode, wherein the planar electrode is an electrode having an area larger than an entire area between the first channel and the second channel in a region where the first channel and the second channel are separated from each other by the porous membrane, and wherein the second channel member is a plate member having a through-hole that serves as the second channel, a holding plate that abuts on the second channel member and closes the through-hole that serves as the second channel is further provided, and the second transparent electrode is formed on an entire surface of the holding plate that abuts on the second channel member.

2. The channel device according to claim 1,
wherein the first channel member is a plate member having a recessed part forming the first channel.

3. The channel device according to claim 1,
wherein the first transparent electrode is formed on an entire surface of the first channel member on which the first channel is formed.

4. The channel device according to claim 1,
wherein the first channel member, or the first channel member and the second channel member are formed of a polymer material, and
the first transparent electrode and the second transparent electrode contain a carbon nanotube.

5. The channel device according to claim 1,
wherein the holding plate is formed of a polymer material, and
the second transparent electrode formed on the entire surface of the holding plate that abuts on the second channel member contains a carbon nanotube.

6. The channel device according to claim 1,
wherein the porous membrane has through-holes arranged in a honeycomb form.

7. The channel device according to claim 1,
wherein the porous membrane is formed of a polymer material.

8. The channel device according to claim 1,
wherein cells are fixed to the porous membrane.

9. The channel device according to claim 8,
wherein the cells fixed to the porous membrane are cells different between one surface and the other surface of the porous membrane.

* * * * *